(12) United States Patent
Bonduelle et al.

(10) Patent No.: US 10,737,254 B2
(45) Date of Patent: *Aug. 11, 2020

(54) OLEFIN METATHESIS METHOD USING A CATALYST CONTAINING SILICON AND MOLYBDENUM

(71) Applicant: IFP Energies Nouvelles, Rueil-Malmaison (FR)

(72) Inventors: Audrey Bonduelle, Francheville (FR); Alexandra Chaumonnot, Lyons (FR); Damien Delcroix, St. Maurice L'Exil (FR); Christophe Vallee, St. Genis Laval (FR); Souad Rafik-Clement, Vourles (FR); Severine Forget, Bourgoin-Jallieu (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 264 days.

This patent is subject to a terminal disclaimer.

(21) Appl. No.: 15/749,297

(22) PCT Filed: Jul. 26, 2016

(86) PCT No.: PCT/EP2016/067832
§ 371 (c)(1),
(2) Date: Jan. 31, 2018

(87) PCT Pub. No.: WO2017/021235
PCT Pub. Date: Feb. 9, 2017

(65) Prior Publication Data
US 2019/0009260 A1 Jan. 10, 2019

(30) Foreign Application Priority Data

Jul. 31, 2015 (FR) ...................................... 15 57370

(51) Int. Cl.
*C07C 6/04* (2006.01)
*B01J 31/22* (2006.01)
(Continued)

(52) U.S. Cl.
CPC ........... *B01J 31/1608* (2013.01); *B01J 23/28* (2013.01); *B01J 23/882* (2013.01); *B01J 27/19* (2013.01);
(Continued)

(58) Field of Classification Search
None
See application file for complete search history.

(56) References Cited

U.S. PATENT DOCUMENTS 2,547,380 A  4/1951  Fleck
6,090,745 A  7/2000  DuBois
(Continued)

FOREIGN PATENT DOCUMENTS

FR  2764211  A1  12/1998
FR  2826880  A1  1/2003
WO  1997047385  A1  12/1997

OTHER PUBLICATIONS

International Search Report PCT/EP2016/067832 dated Oct. 18, 2016.
(Continued)

*Primary Examiner* — Philip Y Louie
(74) *Attorney, Agent, or Firm* — Millen, White, Zelano and Brangian, P.C.

(57) ABSTRACT

The invention relates to a process for the metathesis of olefins implemented with a catalyst comprising a mesoporous matrix and at least the elements molybdenum and silicon, said elements being incorporated into said matrix by
(Continued)

means of at least one precursor comprising molybdenum and silicon and having at least one sequence of Si—O—Mo bonds.

16 Claims, 1 Drawing Sheet

(51) Int. Cl.
*B01J 31/16* (2006.01)
*B01J 35/10* (2006.01)
*B01J 37/02* (2006.01)
*B01J 23/28* (2006.01)
*B01J 27/19* (2006.01)
*B01J 23/882* (2006.01)
*B01J 37/00* (2006.01)
*B01J 37/08* (2006.01)
*C07C 11/02* (2006.01)

(52) U.S. Cl.
CPC ......... *B01J 31/226* (2013.01); *B01J 31/2217* (2013.01); *B01J 35/1019* (2013.01); *B01J 35/1038* (2013.01); *B01J 37/0045* (2013.01); *B01J 37/0201* (2013.01); *B01J 37/0203* (2013.01); *B01J 37/08* (2013.01); *C07C 6/04* (2013.01); *B01J 2231/543* (2013.01); *B01J 2531/64* (2013.01); *B01J 2531/845* (2013.01); *C07C 11/02* (2013.01); *C07C 2523/28* (2013.01); *C07C 2523/882* (2013.01); *C07C 2531/22* (2013.01); *Y02P 20/52* (2015.11)

(56) References Cited

U.S. PATENT DOCUMENTS

| | | |
|---|---|---|
| 6,908,878 B2 | 6/2005 | Euzen |
| 2003/0023125 A1* | 1/2003 | Euzen ............... B01J 23/28 585/646 |
| 2014/0179973 A1* | 6/2014 | Debecker ........... B01J 27/19 585/644 |

OTHER PUBLICATIONS

Giordano N. et al: "Structure and catalytic activity of molybdenum trioxide.silica systems", Revista Portuguesa De Quimica, Lisbon, PT, vol. 19, No. 1-4, Jan. 1, 1977 (Jan. 1, 1977), pp. 31-37, XP008180382, ISSN: 0035-0419.

* cited by examiner

OLEFIN METATHESIS METHOD USING A CATALYST CONTAINING SILICON AND MOLYBDENUM

The present invention relates to a process for the metathesis of olefins using a catalyst prepared from a precursor comprising molybdenum and silicon and having at least one sequence of Si—O—Mo bonds.

PRIOR ART

The metathesis of olefins is an important reaction in various fields of chemistry. In organic synthesis, this reaction, catalyzed by organometallic complexes, is used in order to obtain various high added value molecules. In petrochemistry, the metathesis of olefins is of great practical interest in particular for the rebalancing of light olefins originating from steam cracking, such as ethylene, propylene and butenes. In particular, the cross-metathesis of ethylene with 2-butene in order to produce propylene is a reaction of interest given the increasing use of propylene in the market.

Different types of catalysts are capable of being used in the metathesis reaction. It is possible to use homogeneous catalysts, the constituent elements of which are all soluble in the reaction medium, or heterogeneous catalysts which are insoluble in the reaction medium.

The metathesis of light olefins utilizes heterogeneous catalysts. A known solution is the technology described in U.S. Pat. No. 8,586,813, 2013 which uses a catalyst based on tungsten oxide deposited on a silica support $WO_3/SiO_2$. However, the heterogeneous catalysts based on tungsten operate at a relatively high temperature, generally at a temperature greater than 300° C. and are only moderately active.

Moreover, it is known that metathesis catalysts based on rhenium oxide $Re_2O_7$ such as those described in the publication by Chauvin et al. Journal of Molecular Catalysis 1991, 65, 39 have good activities at temperatures close to ambient temperature. Other catalysts based on molybdenum oxide such as those described in the publication D. P. Debecker et al., J. Catal., 2011, 277, 2, 154 and patents GB 1,164,687 and GB 1,117,968 owned by the company Shell have been also developed. Shell's process uses, for example, catalysts based on molybdenum and cobalt oxides deposited on an aluminium support $CoMoO_4/Al_2O_3$ and doped with phosphorus, as described in U.S. Pat. No. 4,754,099.

One benefit of molybdenum (Mo) is that it is less expensive than Rhenium (Re). In addition, its stability and its activity are intermediate between those of Rhenium (Re) and tungsten (W). In particular, molybdenum can be active starting from ambient temperature.

The preparation of catalysts based on molybdenum oxides ($MoO_3$) is carried out in a standard fashion by impregnation with an aqueous solution of a molybdenum salt or a heteropolyanion containing molybdenum such as for example the isopolyanion ammonium heptamolybdate on a support such as silica, alumina or a porous aluminosilicate. The catalysts prepared from precursors of the ammonium heptamolybdate type however lack activity and stability. Catalysts based on other heteropolyanions such as $H_3PMo_{12}O_{40}$ have been prepared and make it possible to appreciably increase activity, but need further improvement.

Therefore there is still a need to develop new catalysts having improved performances in terms of activity and selectivity for the metathesis reaction of olefins and more particularly for the metathesis between ethylene and 2-butene for the production of propylene.

The Applicant, in his research to improve the performances of the heterogeneous catalysts for the metathesis of olefins, has developed new catalysts for the metathesis reaction of olefins. These catalysts are prepared from a mesoporous matrix and at least one precursor comprising molybdenum and silicon and having at least one sequence of Si—O—Mo bonds. Unexpectedly, it has been found that the use of these types of precursors for the preparation of the catalyst according to the invention improved the activity and the stability of the heterogeneous catalyst obtained for the metathesis reaction of olefins, compared with the catalysts prepared using other precursors of the prior art not having a sequence of Si—O—Mo bonds. The conversion of the olefins is thereby improved. The stability of the catalyst is also improved.

An objective of the present invention is to provide a process for the metathesis of olefins using a catalyst having improved performances in terms of activity and selectivity compared with the use of heterogeneous catalysts of the prior art.

The catalysts according to the invention have the advantage of being able to operate over longer time cycles before regeneration, which has a significant economic impact on the operating costs of the process according to the invention.

SUBJECT OF THE INVENTION

The present invention relates to a process for the metathesis of olefins carried out by bringing the olefins into contact with a catalyst comprising a mesoporous matrix and at least the elements molybdenum and silicon, said elements being incorporated into said matrix by means of at least one precursor comprising molybdenum and silicon and having at least one sequence of Si—O—Mo bonds.

Advantageously, the precursor according to the present invention is a molybdenum coordination complex containing a siloxy ligand and comprising at least one sequence of Si—O—Mo bonds and/or a precursor of heteropolyanion type based on molybdenum comprising at least one sequence of Si—O—Mo bonds.

When the precursor according to the present invention is a molybdenum coordination complex containing a siloxy ligand, it advantageously corresponds to formula (I)

$$Mo_m(=Y)_n(\equiv N)_{n'}(X)_z(=CR_2)_r(OSiR_3)_p \qquad (I)$$

in which the Y groups, identical to or different from each other, can be selected from O, S and NR', the X groups, identical to or different from each other, can be selected from the halides, such as F, Cl, Br, I, the substituted or unsubstituted alkyl, cycloalkyl or aryl, substituted or unsubstituted cyclopentadienyl groups, the alkoxy, aryloxy, siloxy, amide, hydrido, nitro, carboxylate, acetylacetonate, sulphonate, β-diketiminate, iminopyrrolide, amidinate, thiocyanate or $NR_2$—$CS_2^-$ groups, the R groups, identical to or different from each other, can be selected from the substituted or unsubstituted alkyl, cycloalkyl and aryl groups, preferably comprising between 1 and 10 carbon atoms, or from the substituted or unsubstituted alkoxy and aryloxy groups, the R' groups, identical to or different from each other, can be selected from the substituted or unsubstituted alkyl, cycloalkyl and aryl groups, m is equal to 1 or 2, n is comprised between 0 and 4,
n' is comprised between 0 and 2,
z is comprised between 0 and 9,
r is comprised between 0 and 2,
p is comprised between 1 and 10.

Advantageously, when the precursor according to the invention is a precursor of molybdenum coordination complex type containing a siloxy ligand, it corresponds to formula (Ia):

$$Mo_m(\equiv N)_{n'}(OSiR_3)_p \quad (Ia)$$

in which
the R groups, identical to or different from each other, can be selected from the substituted or unsubstituted alkyl, cycloalkyl and aryl groups, preferably comprising between 1 and 10 carbon atoms, or from the substituted or unsubstituted cycloalkyl and aryl groups,
m is equal to 1 or 2,
n' is comprised between 0 and 2,
p is comprised between 1 and 10.

Advantageously, when the precursor according to the invention is a precursor of molybdenum coordination complex type containing a siloxy ligand, it corresponds to formula (Ib)

$$Mo_m(=O)_n(OSiR_3)_p \quad (Ib)$$

in which
the R groups, identical to or different from each other, can be selected from the substituted or unsubstituted alkyl, cycloalkyl and aryl groups, preferably comprising between 1 and 10 carbon atoms, or from the substituted or unsubstituted alkoxy and aryloxy groups,
m is equal to 1 or 2,
n is comprised between 0 and 4,
p is comprised between 1 and 10.

According to the invention, the precursor of molybdenum coordination complex type containing a siloxy ligand can also contain in its coordination sphere one or more L-type ligands, optionally polydentate. The L-type ligand can be selected from the phosphorus-containing compounds such as the phosphines, phosphinites, phosphonites, phosphites, the oxygen-containing compounds such as the ethers, the nitrogen-containing compounds such as the amines, the nitrogen-containing aromatic compounds such as pyridine and/or phenantroline, and/or the sulphur-containing compounds such as the thioethers.

The precursor of molybdenum coordination complex type containing a siloxy ligand can for example be selected from the following compounds: $MoO(OSiMe_3)CN(CS_2-NEt_2)_2$, $Mo(=N-(2,6-di-iPrC_6H_3))(tBu)(=CHtBu)(OSi(OtBu)_3)$, $Mo(=S)(=NiPr)(OSitBu_3)_2$, $Mo(=O)(OSitBu_3)_4$, $Mo(EN)(OSiPh_3)_3(C_6H_5N)$ or $Mo_2(OSiMe_3)_6$.

When the precursor according to the present invention is a precursor of heteropolyanion type based on molybdenum, it advantageously corresponds to formula (II)

$$(Si_xMo_mM_bO_yH_h)^{q-}\cdot nH_2O \quad (II)$$

in which,
x is at least equal to 1,
m is greater than or equal to 1,
b is greater than or equal to 0,
m+b greater than or equal to 5,
y is greater than or equal to 20,
h is comprised between 0 and 12,
q is comprised between 1 and 20,
n is comprised between 0 and 200,
x, m, b, y, h, n and q being integers, M being a metallic element other than silicon and molybdenum.

Advantageously, when the precursor according to the invention is a precursor of heteropolyanion type, it corresponds to formula (II):

$$(Si_xMo_mM_bO_yH_h)^{q-}\cdot nH_2O \quad (II)$$

in which,
x is equal to 1 or 2,
m is greater than or equal to 1,
b is greater than or equal to 0,
m+b greater than or equal to 5,
y is comprised between 20 and 50,
h is comprised between 0 and 12,
q is comprised between 3 and 12,
n is comprised between 0 and 200;
x, m, b, y, h, n and q being integers, M being a metallic element selected from aluminium, zinc, nickel, cobalt, tungsten, vanadium, niobium, tantalum, iron and copper, preferably M is a metallic element selected from aluminium, cobalt and tungsten, more preferably from aluminium and cobalt and yet more preferably, the metallic element M is cobalt.

The precursor of heteropolyanion type based on molybdenum corresponding to formula (II) can be incorporated in the mesoporous matrix in the form of salts or in the form of an acid. In the case where the precursor of heteropolyanion type is incorporated in the form of an acid, the charge $q^-$ is compensated for by protons $H^+$. When the heteropolyanion is introduced in the form of salt, the counter-ions of the salt of the heteropolyanion are selected from all the cations known to a person skilled in the art. By way of example the proton, the ammoniums, phosphoniums, alkalis, alkaline-earths, transition elements, etc. can be mentioned. The salt can comprise a mixture of the same cation or of different cations. The precursor of molybdenum coordination complex type containing a siloxy ligand corresponding to formula (I), (Ia), or (Ib), is incorporated of by its chemical nature in the neutral form.

One or more precursors of heteropolyanion type based on molybdenum corresponding to formula (II) can be used. One or more precursors of molybdenum coordination complex type containing a siloxy ligand corresponding to formula (I), (Ia), or (Ib), can be used.

The precursor of heteropolyanion type based on molybdenum can contain one or more metallic elements M selected from aluminium, zinc, nickel, cobalt, tungsten, vanadium, niobium, tantalum, iron and copper, in substitution for one or more molybdenum atoms contained in said heteropolyanion precursor of formulae described above. Preferably, the metallic element M is selected from aluminium, cobalt and tungsten, more preferably from aluminium and cobalt and yet more preferably, the metallic element M is cobalt.

When the precursor of heteropolyanion type based on molybdenum used in the preparation of the catalyst utilized in the metathesis process according to the invention does not contain a metallic element M, it is advantageously selected from the group formed by a Strandberg heteropolyanion of formula $Si_2Mo_5O_{23}^{8-}\cdot nH_2O$, an Anderson heteropolyanion of formula $SiMo_6O_{24}^{8-}$, a Keggin heteropolyanion of formula $SiMo_{12}O_{40}^{4-}\cdot nH_2O$, a lacunary Keggin heteropolyanion of formula $SiMo_{11}O_{39}^{8-}\cdot nH_2O$, a lacunary Keggin heteropolyanion of formula $SiMo_9O_{34}^{10-}\cdot nH_2O$, a Dawson heteropolyanion of formula $Si_2Mo_{18}O_{62}^{8-}\cdot nH_2O$, a Preyssler heteropolyanion of formula $Si_5Mo_{30}O_{110}^{20-}\cdot nH_2O$.

When the precursor of heteropolyanion type based on molybdenum used in the preparation of the catalyst utilized in the metathesis process according to the invention contains a metallic element M other than molybdenum and silicon, M preferably being the cobalt, it is advantageously selected from the group formed by a Strandberg heteropolyanion of formula $Si_2Mo_4CoO_{23}^{12-}.nH_2O$, an Anderson heteropolyanion of formula $SiMo_5CoO_{24}^{12-}.nH_2O$, a Keggin heteropolyanion of formula $SiMo_{11}CoO_{40}^{8-}.nH_2O$, a lacunary Keggin heteropolyanion of formula $SiMo_{10}CoO_{39}^{12-}.nH_2O$, a lacunary Keggin heteropolyanion of formula $SiMo_8CoO_{34}^{14-}.nH_2O$, a Dawson heteropolyanion of formula $Si_2Mo_{17}CoO_{62}^{12-}.nH_2O$, a Preyssler heteropolyanion of formula $Si_5Mo_{29}CoO_{110}^{24-}.nH_2O$, (the preparation of which is precisely described in application FR 2,764,211).

The mesoporous matrix according to the invention is advantageously a matrix based on the oxide of at least one element X selected from silicon, aluminium, titanium, zirconium, magnesium, lanthanum, cerium and mixtures thereof. Preferably, the element X is aluminium or a mixture of aluminium and silicon. More preferably, the element X is aluminium.

Said matrix based on oxide described as mesoporous is understood to mean according to the present invention a matrix comprising pores the size of which varies between 2 and 50 nm according to the IUPAC classification (K. S. W. Sing, D. H. Everett, W. R. A. Haul, L. Moscou, J. Pierotti, J. Rouquerol, T. Siemieniewska, Pure Appl. Chem. 1985, 57, 603), and/or a mesostructured mesoporous matrix, i.e. having mesopores of uniform size and distributed periodically through said matrix and/or a matrix with hierarchical porosity, i.e. comprising micropores and/or macropores in addition to the mesopores.

Preferentially, a mesoporous matrix is used based on aluminium oxide having a specific surface area of 10 to 500 m²/g, and preferably at least 50 m²/g, and a pore volume of at least 0.1 ml/g, and preferably a pore volume comprised between 0.3 and 1.2 ml/g according to the BET method.

The catalyst used according to the invention comprises a content by weight of molybdenum element provided by the precursor of formula (I), (Ia), or (Ib) and/or of formula (II) according to the invention comprised between 1 and 40%, preferably between 2 and 30%, preferably between 2 and 20%, expressed as a percentage by weight of molybdenum with respect to the weight of the mesoporous matrix.

The catalyst used according to the invention comprises a content by weight of silicon element provided by the precursor of formula (I), (Ia), or (Ib) and/or of formula (II) according to the invention comprised between 0.01 and 50%, preferably between 0.02 and 35%, preferably between 0.02 and 25% expressed as a percentage by weight of aluminium element with respect to the weight of the mesoporous matrix.

Preferably, when the precursor is a molybdenum coordination complex containing a siloxy ligand according to the invention, the content by weight of silicon element provided by the precursor according to the invention is comprised between 1 and 25% expressed as a percentage by weight of silicon element with respect to the weight of the mesoporous matrix.

Preferably, when the precursor is a heteropolyanion based on molybdenum according to the invention, the content by weight of silicon element provided by the precursor according to the invention is comprised between 0.02 and 10% expressed as a percentage by weight of silicon element with respect to the weight of the mesoporous matrix.

Preferably, when the precursor is a mixture of precursors, the content by weight of silicon element provided by the precursor according to the invention corresponds to the sum of the contents by weight of silicon element provided by each of the precursors.

The catalyst according to the invention can be prepared according to the methods known to a person skilled in the art.

In a variant of the process for the preparation of the catalyst used according to the invention, the precursor comprising molybdenum and silicon and having at least one sequence of Si—O—Mo bonds is deposited on the surface of a preformed mesoporous matrix based on oxide.

The preformed mesoporous matrix can be commercial or synthesized according to the methods known to a person skilled in the art, in particular by use of the "traditional" inorganic synthesis methods: precipitation/gelation from salts under mild temperature and pressure conditions; or "modern" metallo-organic: precipitation/gelation from alkoxides under mild temperature and pressure conditions. In the remainder of the text and for the sake of clarity, these methods are simply called "sol-gel".

The preformed mesoporous matrix can be in the form of powder or formed, for example in the form of pelletized, crushed or sieved powder, granules, tablets, beads, wheels, spheres or extrudates (cylinders which can be hollow or not, multilobed cylinders with 2, 3, 4 or 5 lobes for example, twisted cylinders), or rings, etc.

The deposition or incorporation of the precursor comprising molybdenum and silicon and having at least one sequence of Si—O—Mo bonds on the mesoporous matrix can be done before, during or after the forming of the mesoporous matrix.

The deposition or incorporation of the precursors according to the invention on the mesoporous matrix can be carried out by methods called dry impregnation, impregnation in excess, CVD (chemical vapour deposition), CLD (chemical liquid deposition), etc. described for example in "Catalysis by transition metal sulphides, from molecular theory to industrial application, by Hervé Toulhouat and Pascal Raybaud, p137" can be used.

The catalyst can be prepared by dry impregnation according to the process comprising the following stages:

a) solubilization of the precursor comprising molybdenum and silicon and having at least one sequence of Si—O—Mo bonds, of formula (I), (Ia), or (Ib), and/or of formula (II) in a volume of solution corresponding to the pore volume of a preformed mesoporous matrix based on oxide, b) impregnation of the preformed mesoporous matrix based on oxide with the solution obtained in stage a), optional maturation of the solid thus obtained, c) optional stage of drying, calcination and/or steam treatment of the solid obtained at the end of stage b), at a pressure greater than or equal to 0.1 MPa or less than or equal to 0.1 MPa, in a temperature range from 50° C. to 1000° C., d) stage of thermal activation of the solid obtained at the end of stage c), at a pressure greater than or equal to 0.1 MPa or less than or equal to 0.1 MPa, in a temperature range from 100° C. to 1000° C.

The maturation optionally implemented in stage b) is carried out in a controlled atmosphere and at a controlled temperature so as to promote the dispersion of said precursor over the entire surface of the preformed mesoporous matrix based on oxide. Advantageously, the maturation is carried out at a temperature comprised between 20 and 120° C. and a pressure comprised between 0.01 and 1 MPa.

Stages c) and/or d) can be carried out under an oxidizing, reducing or neutral atmosphere.

Preferably, optional drying stage c) is carried out in a temperature range from 20° C. to 200° C., preferably from 50° C. to 150° C. and preferably from 100° C. to 130° C. during a period of less than 72 h and preferably less than 24 h.

Preferably, thermal activation stage d) is carried out under a neutral atmosphere at atmospheric pressure in a temperature range from 200° C. to 800° C., preferably from 350° C. to 650° C. Preferably, the neutral atmosphere is nitrogen in a flow rate range from 0.01 to 20 Nl/h per gram of solid obtained at the end of stage c), preferably from 0.1 to 10 Nl/h per gram of solid obtained at the end of stage (c).

The catalyst can be prepared by impregnation in excess, according to the process comprising the following stages:

a') solubilization of the precursor comprising molybdenum and silicon and having at least one sequence of Si—O—Mo bonds, of formula (I), (Ia), or (Ib), and/or of formula (II) in a volume of solution, corresponding to between 1.5 and 20 times the pore volume of the preformed mesoporous matrix based on oxide, b') impregnation of the preformed mesoporous matrix based on oxide, with the solution obtained in stage a'), filtration and recovery of the solid, optional maturation of the solid thus obtained, c') optional stage of drying, calcination and/or steam treatment of the solid obtained at the end of stage b') at a pressure greater than or equal to 0.1 MPa or less than or equal to 0.1 MPa, in a temperature range from 50° C. to 1000° C., d') stage of thermal activation of the solid obtained at the end of stage c') at a pressure greater than or equal to 0.1 MPa or less than or equal to 0.1 MPa, in a temperature range from 100° C. to 1000° C.

The maturation optionally implemented in stage b') is carried out in a controlled atmosphere and at a controlled temperature so as to promote the dispersion of said precursor over the entire surface of the preformed mesoporous matrix based on oxide. Advantageously, the maturation is carried out at a temperature comprised between 20 and 120° C. and a pressure comprised between 0.01 and 1 MPa.

Preferably, the solubilization of the precursor comprising molybdenum and silicon and having at least one sequence of Si—O—Mo bonds, of formula (I), (Ia),or (Ib), and/or of formula (II) in the stage a) is carried out in a volume of solution corresponding to between 2 and 10 times the pore volume of the preformed mesoporous matrix based on oxide.

Stages c') and/or d') can be carried out under an oxidizing, reducing or neutral atmosphere.

Preferably, optional drying stage c') is carried out in a temperature range from 20° C. to 200° C., preferably from 50° C. to 150° C. and preferably from 100° C. to 130° C. during a period of less than 72 h and preferably less than 24 h.

Preferably, thermal activation stage d') is carried out under a neutral atmosphere at atmospheric pressure in a temperature range from 200° C. to 800° C., preferably from 350° C. to 650° C. Preferably, the neutral atmosphere is nitrogen in a flow rate range from 0.01 to 10 Nl/h per gram of solid obtained at the end of stage c'), preferably from 0.1 to 5 Nl/h per gram of solid obtained at the end of stage c').

Organic compounds, called organic additives, can also be used during the preparation of the catalyst according to the invention. At least one organic additive can be introduced by impregnation onto the mesoporous matrix before the stage of impregnation with the precursor (stage b or b'), by co-impregnation with the precursor or post-impregnation after impregnation with the precursor.

The organic compounds or additives used are selected from chelating agents, non-chelating agents, reducing agents and additives known to a person skilled in the art.

Said organic compounds or additives are advantageously selected from mono-, di- or polyalcohols optionally etherified, carboxylic acids (citric acid, acetic acid, etc.), sugars, the non-cyclic mono, di or polysaccharides such as glucose, fructose, maltose, lactose or sucrose, cyclic or non-cyclic esters, cyclic or non-cyclic ethers, ketones, compounds combining several of these functions (ketones, carboxylic acids, ethers, esters, alcohols, amines, etc.), crown ethers, cyclodextrins and compounds containing at least sulphur, or phosphorus or nitrogen such as nitriloacetic acid, ethylenediaminetetraacetic acid, or diethylenetriamine, amino acids and zwitterrionic compounds, used alone or in a mixture.

The impregnation and/or of solubilization solvent can be selected from any solvent known to a person skilled in the art such as water, organic solvents, ionic liquids etc. A mixture of solvents can also be used.

When the precursor is a heteropolyanion based on molybdenum according to the invention, water or a protic polar solvent is preferably used such as the alcohols: ethanol, methanol, etc.

When the precursor is a molybdenum coordination complex containing a siloxy ligand, an aprotic organic solvent is preferably used such as the hydrocarbons: pentane, heptane, cyclohexane, the aromatics: toluene, xylene etc. the ethers: diethylether, tetrahydrofuran (THF) etc.

When a precursor of heteropolyanion type based on molybdenum and a molybdenum coordination complex containing a siloxy ligand are used together, an aprotic organic solvent is preferably used, such as dimethylsulphoxide (DMSO), dimethylformamide (DMF) or acetonitrile.

One or more other metallic elements can also be introduced into the composition of the catalyst used in the process according to the invention. This metallic element can be selected from zinc, nickel, cobalt, tungsten, vanadium, niobium, tantalum, iron and copper. This metallic element is introduced at a content comprised between 0.01 and 10%, and preferably between 0.02 and 5% expressed in % by weight of metal with respect to the weight of the mesoporous matrix based on oxide.

This metallic element can be provided by a compound selected from the salts and/or oxides of zinc, nickel, cobalt, tungsten, vanadium, niobium, tantalum, iron and copper, preferably the salts and/or oxides of zinc, nickel, cobalt, tungsten. Preferably, the compound is a cobalt salt, carboxylate, alkoxide or oxide. Preferably, the compound is $Co(NO_3)_2$ or CoO. Very preferably, the compound is $Co(NO_3)_2$.

This compound can be introduced by impregnation onto the mesoporous matrix before impregnation with the precursor(s) according to the invention comprising molybdenum and silicon and having at least one sequence of Si—O—Mo bonds, of formula (I), (Ia), or (Ib), and/or of formula (II) by co-impregnation with the precursor(s) according to the invention The deposition or the incorporation of the precursor(s) comprising molybdenum and silicon and having at least one sequence of Si—O—Mo bonds, of formula (I), (Ia), or (Ib), and/or of formula (II) on the mesoporous matrix can also be done directly during the synthesis of the mesoporous matrix based on oxide.

The synthesis methods used can be hydrolytic or non hydrolytic "sol-gel" methods by precipitation or by evaporation. The evaporation methods can require the use of a specific synthesis process such as spray-drying, the deposition of thin films, etc.

In the particular case of a hydrolytic sol-gel synthesis by spray-drying leading to a catalyst having a mesostructured matrix based on oxide being obtained, the catalyst used in the process according to the invention can be prepared according to the process comprising the following stages:

a1) solubilization of the precursor comprising molybdenum and silicon and having at least one sequence of Si—O—Mo bonds, of formula (I), (Ia), or (Ib), and/or of formula (II) and the precursors of the mesoporous matrix based on oxide of at least one element X in an aqueous or hydro-organic solution in the presence of a pore-forming agent so as to form a colloidal solution, b1) spray-drying said colloidal solution so as to obtain spherical solid elemental particles incorporating the mesostructured matrix based on oxide and the precursor comprising molybdenum and silicon and having at least one sequence of Si—O—Mo bonds of formula (I), (Ia), or (Ib), and/or of formula (II), c1) optional stage of drying, calcination and/or steam treatment of the solid particles obtained at the end of stage b1) at a pressure greater than or equal to 0.1 MPa or less than or equal to 0.1 MPa, d1) stage of thermal activation of the dry solid particles at the end of stage c1), at a pressure greater than or equal to 1 bar or less than or equal to 0.1 MPa, in a temperature range from 100 to 1000° C.

Preferably, the optional drying stage c1) is carried out in a temperature range from 20 to 200° C., preferably from 50° C. to 150° C. and preferably from 100° C. to 130° C. during a period of less than 72 h and preferably less than 24 h. Stage c1) can be carried out under an oxidizing, reducing or neutral atmosphere.

The stage of thermal activation d1) can be carried out under an oxidizing, reducing or neutral atmosphere.

Preferably, thermal activation stage d1) is carried out under a neutral atmosphere at atmospheric pressure in a temperature range from 200 to 800° and preferably from 350 to 650° C. Preferably, the neutral atmosphere is nitrogen in a flow rate range from 0.01 to 10 Nl/h per gram of solid obtained at the end of stage c1), preferably from 0.1 to 5 Nl/h per gram of solid obtained at the end of stage c1).

By hydro-organic solution is meant a solution of a mixture of water and an organic solvent. Preferably the hydro-organic solution is a hydro-ethanolic solution.

The pore-forming agent used in stage a1) is for example an ionic or non-ionic surfactant compound or a mixture of the two.

The precursor(s) of the mesoporous matrix are precursors of the matrix based on an oxide of at least one element X selected from silicon, aluminium, titanium, zirconium and mixtures thereof. This/these precursor(s) can be any compound comprising the element X and capable of releasing this element in solution in reactive form. Thus, the precursor(s) of at least said element X of the matrix is(are) advantageously an inorganic salt of said element X of formula $XZ_n$, (n=3 or 4), Z being a halogen, the $NO_3$ or a perchlorate group, preferably Z is chlorine. The precursor(s) of at least said considered element X can also be one of the alkoxide precursor(s) of formula X(OR)n where R=ethyl, isopropyl, n-butyl, s-butyl, t-butyl, etc. or a chelated precursor such as $X(C_5H_8O_2)n$, with n=3 or 4. The precursor(s) of at least said considered element X can also be one (or more) oxide(s) or one (or more) hydroxides of said element X.

In the preferred case where X is aluminium or a mixture of aluminium and silicon, the silica and/or alumina precursors are precursors of inorganic oxides well known to a person skilled in the art. The silica precursor is obtained from any source of silica and advantageously from a sodium silicate precursor of formula $Na_2SiO_3$, from a chlorinated precursor of formula $SiCl_4$, from an alkoxide precursor of formula $Si(OR)_4$ where R=H, methyl, ethyl or from a chloroalkoxide precursor of formula $Si(OR)_{4-a}Cl_a$ where R=H, methyl, ethyl, a being comprised between 0 and 4. The silica precursor can also advantageously be an alkoxide precursor of formula $Si(OR)_{4-a}R'_a$ where R=H, methyl, ethyl and R' is an alkyl chain or a functionalized alkyl chain, for example by a thiol, amino, β-diketone, sulphonic acid group, a being comprised between 0 and 4. A preferred silica precursor is tetraethylorthosilicate (TEOS). The alumina precursor is advantageously an inorganic salt of aluminium of formula $AlZ_3$, Z being a halogen or the $NO_3$ group. Preferably, Z is chlorine. The alumina precursor can also be an inorganic salt of aluminium of formula $Al_2Z'_3$, Z' being the sulphate group $SO_4$. The alumina precursor can be also an alkoxide precursor of formula $Al(OR")_3$ or R"=ethyl, isopropyl, n-butyl, s-butyl or t-butyl or a chelated precursor such as aluminium acetylacetonate ($Al(CH_7O_2)_3$). The alumina precursor can also be an aluminium oxide or hydroxide, for example AlOONa.

In the case where the catalyst used in the process according to the invention is obtained in the form of powder at the end of the different processes of preparation disclosed above, the latter can be formed according to the methods well known to a person skilled in the art. Thus, it can be in the form of pelletized, crushed or sieved powder, granules, tablets, beads, wheels, spheres or extrudates (cylinders which can be hollow or not, multilobed cylinders with 2, 3, 4 or 5 lobes for example, twisted cylinders), or rings, etc. Preferably, said catalyst is formed as extrudates During said forming operation, the catalyst used in the process according to the invention can optionally be mixed with at least one porous oxide material acting as a binder so as to generate the physical properties of the catalyst suitable for the process according to the invention (mechanical strength, attrition resistance etc.).

Said porous oxide material is preferentially a porous oxide material selected from the group formed by alumina, silica, silica-alumina, magnesia, clays, titanium oxide, zirconium oxide, lanthanum oxide, cerium oxide, aluminium phosphates and a mixture of at least two of the oxides mentioned above. Said porous oxide material can also be selected from alumina-boron oxide, alumina-titanium oxide, alumina-zirconia and titanium-zirconium oxide mixtures. The aluminates, for example magnesium, calcium, barium, manganese, iron, cobalt, nickel, copper and zinc aluminates, as well as mixed aluminates for example those containing at least two of the metals mentioned above, are advantageously used as porous oxide material. Titanates can also be used, for example zinc, nickel, cobalt titanates. Mixtures of alumina and silica and mixtures of alumina with other compounds such as the group VIB elements, phosphorus, fluorine or boron can also advantageously be used. It is also possible to use simple, synthetic or natural clays of the dioctahedral phyllosilicate 2:1 type or trioctahedral phyllosilicate 3:1 type such as kaolinite, antigorite, chrysotile, montmorillonite, beidellite, vermiculite, talc, hectorite, saponite, laponite. These clays can optionally be delaminated. Mixtures of alumina and clay and mixtures of silica-alumina and clay can also be advantageously used. Various mixtures using at least two of the compounds mentioned above are also suitable to act as binders.

Optionally, at least one organic adjuvant is also mixed during said forming stage. The presence of said organic adjuvant facilitates forming by extrusion. Said organic adjuvant can advantageously be selected from polyvinylpyrrolidones, cellulose polymers and derivatives thereof, preferably selected from cellulose ethers such as for example Methocel, marketed by the Dow Chemical company, polyvinyl alcohols, polyethylene glycols, polyacrylamides, polysaccharides, natural polymers and derivatives thereof such as for example the alginates, polyesters, polyamides and aromatic polyamides, polyethers, poly(arylether)s, polyurethanes, polysulphones such as polysulphone ethers, heterocyclic polymers, preferably selected from polyimides, polyimide ethers, polyimide esters, polyimide amides, and polybenzimidazoles The proportion of said organic adjuvant is advantageously comprised between 0 and 20% by weight, preferably between 0 and 10% by weight and preferably between 0 and 7% by weight, with respect to the total weight of the mesoporous matrix formed.

Metathesis Reaction

The process for the metathesis of olefins carried out by bringing the olefins into contact with the catalyst defined above, is advantageously carried out at a temperature comprised between 0 and 500° C., preferably comprised between 0 and 400° C., more preferably between 20 and 350° C. and yet more preferably between 30 and 350° C.

The metathesis reaction of olefins can be carried out in gas phase or in liquid phase. The reaction can be carried out in batch mode, in a stirred reactor, or in continuous mode, by passing the olefin reagent(s) through a fixed bed, a moving bed or a fluidized bed of catalyst.

The pressure at which the process according to the invention is carried out is not critical. However, for an operation in liquid phase, it is advantageous to maintain a pressure at least equal to the vapour pressure of the reaction mixture at the temperature of the reaction.

The reaction is preferably carried out in the absence of solvents. However, the reaction can be carried out in the presence of a solvent such as a hydrocarbon, or a halogenated, aliphatic, cyclanic or aromatic hydrocarbon.

Olefins capable of reacting by metathesis in the process according to the invention can be linear olefins corresponding to general formula $R^1R^2C=CR^3R^4$, where $R^1$, $R^2$, $R^3$ and $R^4$, identical or different, are hydrogen or a hydrocarbyl radical with 1 to 20 carbon atoms, or olefins with a cyclic structure, the ring comprising from 3 to 20 carbon atoms.

An olefin can either be reacted by itself, or several olefins can be reacted together in a mixture. The process according to the invention is in particular the cross-metathesis reaction of ethylene with 2-butene in order to produce propylene, or the reverse reaction converting propylene to a mixture of ethylene and 2-butene.

Other olefins capable of reacting by metathesis are the monoolefins or polyolefins, linear or cyclic, bearing functional groups such as for example halogen or ester groups. The process can also utilize, in co-metathesis a mixture of the above-mentioned olefins.

In the case of the production of propylene by metathesis between ethylene and 2-butene, the 2-butene can preferably originate from a dimerization reaction of ethylene in the presence of a homogeneous or heterogeneous catalyst known to a person skilled in the art. For example, the 2-butene can originate from a dimerization of ethylene in the presence of a nickel complex of the $NiCl_2(PBu_3)_2$ type producing a mixture of 1-butene and 2-butene by homogeneous catalysis. For example, the 2-butene can originate from a dimerization of ethylene in the presence of a heterogeneous catalyst based on nickel of the $NiSO_4/Al_2O_3$ type producing a mixture of 1-butene and 2-butene by heterogeneous catalysis.

In the case of the production of propylene by metathesis between ethylene and a mixture of 2-butene and 1-butene, a catalyst for the isomerization of 1-butene to 2-butene is preferably used in order to maximize the propylene yield. For example, an oxide catalyst of the MgO or $K_2O$ type can be used to isomerize the 1-butene to 2-butene.

Ethylene can advantageously be obtained by the dehydration of biosourced ethanol by any dehydration method known to a person skilled in the art in order to allow the production of biosourced propylene.

EXAMPLES

In the examples, the precursor of complex coordination type containing a siloxy ligand, tris(triphenylsilyloxy)molybdenum nitride stabilized with pyridine Mo(≡N)(OSiPh$_3$)$_3$(Pyridine) and the precursors of heteropolyanion type phosphomolybdic acid $PMo_{12}O_{40}^{3-}.3H^+$ and silicomolybdic acid $SiMo_{12}O_{40}^{4-}.4H^+$ are commercially available.

The heteropolyanion precursor cobaltosilicomolybdic acid $SiCoMo_{11}O_{40}^{4-}.4H^+$ is synthetized according to a method described in patent application FR 2,764,211.

Example 1A (Not According to the Invention): Preparation of 6.7% $Mo/Al_2O_3$ by Dry Impregnation with a Solution with $PMo_{12}O_{40}^{3-}.3H^+.30H_2O$ 1.5 g of $PMo_{12}O_{40}^{3-}.3H^+.30H_2O$ is dissolved at 60° C. in 7.3 ml of distilled water. On complete dissolution, an alumina ($S_{BET}$=198 m$^2$/g, $V_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Example 1B (According to the Invention): Preparation of 6.7% $Mo/Al_2O_3$ by Dry Impregnationtion with $SiMo_{12}O_{40}^{4-}.4H^+.28H_2O$ 1.4 g of $SiMo_{12}O_{40}^{4-}.4H^+.28H_2O$ is dissolved at 60° C. in 7.3 ml of distilled water. On complete dissolution, an alumina ($S_{BET}$=198 m$^2$/g, $V_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Example 1C (According to the Invention): Preparation of 6.1% Mo+0.3% $Co/Al_2O_3$ by Dry Impregnation with a Solution of $SiCoMo_{11}O_{40}^{4-}.4H^+.28H_2O$ 1.4 g of $SiCoMo_{11}O_{40}^{4-}.4H^+.28H_2O$ is dissolved at 60° C. in 7.3 ml of distilled water. An alumina ($S_{BET}$=198 m$^2$/g, $V_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Example 1D (According to the Invention): Preparation of 6.7% Mo+0.9% Co/Al$_2$O$_3$ by Dry Impregnation with a Solution of SiMo$_{12}$O$_{40}$$^{4-}$.4H$^+$.28H$_2$O and of Co(NO$_3$)$_2$ 1.4 g of SiMo$_{12}$O$_{40}$$^{4-}$.4H$^+$.28H$_2$O and 0.69 g of Co(NO$_3$)$_2$.6H$_2$O are dissolved at 60° C. in 7.3 ml of distilled water. An alumina (S$_{BET}$=198 m$^2$/g, V$_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Example 1E (According to the Invention): Preparation of 6.7% Mo/Al$_2$O$_3$ by Dry Impregnation with a Solution of Mo(≡N)(OSiPh$_3$)$_3$(Pyridine)

11.6 g of Mo(≡N)(OSiPh$_3$)$_3$(Pyridine) is dissolved at 60° C. in 7.3 ml of distilled water. An alumina (S$_{BET}$=198 m$^2$/g, V$_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Example 1F (According to the Invention): Preparation of 6.7% Mo/Al$_2$O$_3$ by Dry Impregnation with a Solution of SiMo$_{12}$O$_{40}$$^{4-}$.4H$^+$.28H$_2$O and of Mo(≡N)(OSiPh$_3$)$_3$(Pyridine)

0.7 g of SiMo$_{12}$O$_{40}$$^{4-}$.4H$^+$.28H$_2$O and 5.8 g of Mo(≡N)(OSiPh$_3$)$_3$(Pyridine) are dissolved at 60° C. in 7.3 ml of distilled water. An alumina (S$_{BET}$=198 m$^2$/g, V$_p$=0.47 ml/g) is impregnated with this solution. The solid obtained is matured for 24 h at 25° C. under air. The resulting solid is dried in an oven at 120° C. for 24 h then activated under nitrogen at 550° C. for 2 h.

Figure 1:
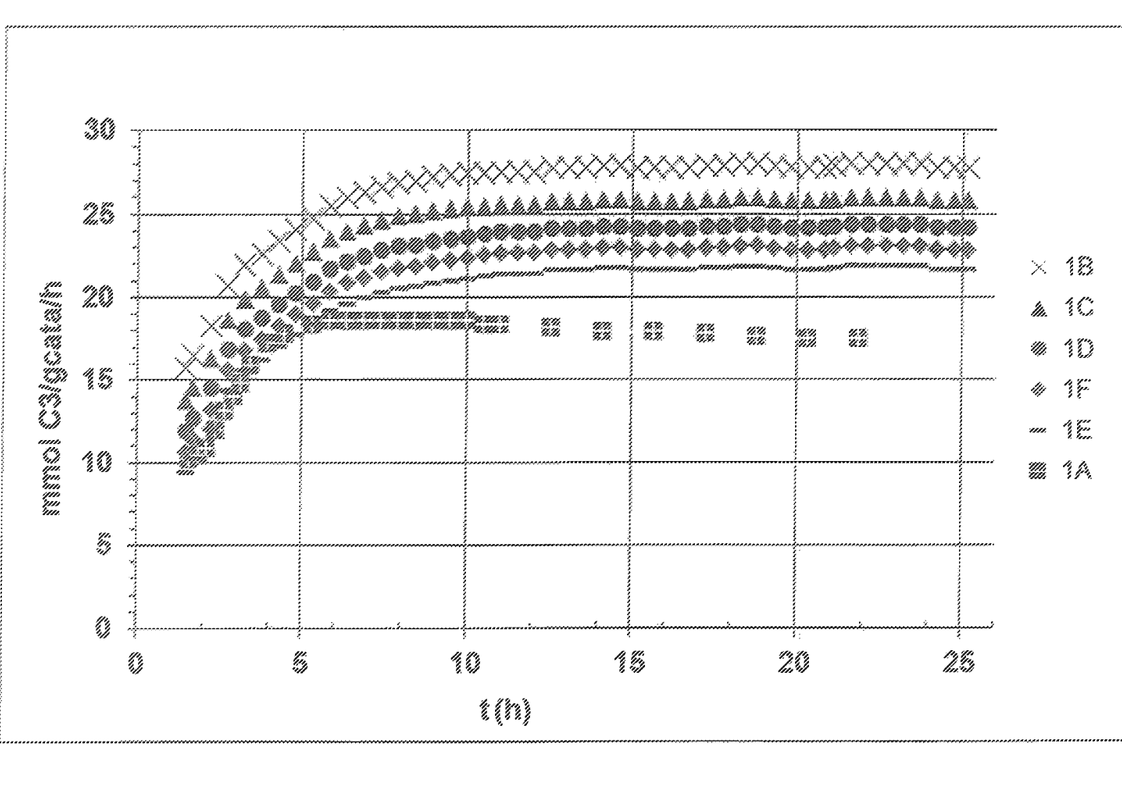
FIG. 1 represents a graph of catalyst productivity of comparative catalysts and inventive catalysts.

Example 2: Metathesis of Propylene to Ethylene and 2-Butene 2 g of catalyst prepared in Example 1A to 1F is mixed in a proportion of 50% by weight with silicon carbide (SiC) in a double-jacketed fixed bed reactor. The heat transfer fluid of the double jacket is heated to 70° C. Pure propylene is conveyed to the reactor by means of a Gilson pump and the pressure is set at 4.5 MPa. The productivity of the catalysts expressed in millimole of propylene consumed per gram of catalyst and per hour is quantified as a function of time denoted t (in hours denoted h) in the FIGURE.

The activity of all the catalysts 1B to 1F according to the invention prepared by impregnation with precursors based on molybdenum having Si—O—Mo bonds is greater than the activity of catalyst 1A not according to the invention and prepared by impregnation with a precursor based on molybdenum not having Si—O—Mo bonds: PMo$_{12}$O$_{40}$$^{3-}$.3H$^+$.30H$_2$O.

The stability of catalysts 1B to 1F according to the invention is better than the stability of catalyst 1A not according to the invention.

The invention claimed is:

1. A process comprising metathesis of olefins carried out by bringing the olefins into contact with a catalyst comprising a mesoporous matrix and at least the elements molybdenum and silicon, said elements being incorporated into said matrix using at least one precursor comprising molybdenum and silicon, having at least one sequence of Si—O—Mo bonds and a siloxy ligand, that is a molybdenum coordination complex containing a siloxy ligand, of formula (I):

Mo$_m$(=Y)$_n$(≡N)$_{n'}$(X)$_z$(=CR$_2$)$_r$(OSiR$_3$)$_p$ (I)

in which
the Y groups, identical to or different from each other, are O, S or NR',
the X groups, identical to or different from each other, are a halide, a substituted or unsubstituted alkyl, cycloalkyl or aryl, substituted or unsubstituted cyclopentadienyl group, or an alkoxy, aryloxy, siloxy, amide, hydrido, nitro, carboxylate, acetylacetonate, sulphonate, β-diketiminate, iminopyrrolide, amidinate, thiocyanate or NR$_2$—CS$_2$$^-$ group,
the R groups, identical to or different from each other, are a substituted or unsubstituted alkyl, cycloalkyl and aryl group, or a substituted or unsubstituted alkoxy and aryloxy group,
the R' groups, identical to or different from each other, are a substituted or unsubstituted alkyl, cycloalkyl and aryl group,
m is equal to 1 or 2,
n is 0 to 4,
n' is 0 to 2,
z is 0 to 9,
r is 0 to 2, and
p is 1 to 10.

2. The process according to claim 1, wherein the X groups are F, Cl, Br, or I,
and the R groups are substituted or unsubstituted alkyl, cycloalkyl and aryl groups having 1 to 10 carbon atoms.

3. The process according to claim 1, wherein the precursor is of formula (Ia):

Mo$_m$(≡N)$_{n'}$(OSiR$_3$)$_p$ (Ia)

in which
the R groups, identical to or different from each other, are substituted or unsubstituted alkyl, cycloalkyl and aryl groups or substituted or unsubstituted cycloalkyl and aryl groups,
m is equal to 1 or 2,
n' is 0 to 2, and
p is 1 to 10.

4. The process according to claim 1, wherein the precursor is of formula (Ib)

Mo$_m$(=O)$_n$(OSiR$_3$)$_p$ (Ib)

in which
the R groups, identical to or different from each other, are substituted or unsubstituted alkyl, cycloalkyl and aryl groups or substituted or unsubstituted alkoxy and aryloxy groups,
m is equal to 1 or 2,
n is 0 to 4, and
p is 1 to 10.

5. The process according to claim 1, wherein the molybdenum coordination complex containing a siloxy ligand contains in its coordination sphere one or more optionally polydentate L-type ligands that are phosphorus-containing compounds, oxygen-containing compounds, nitrogen-containing compounds, nitrogen-containing aromatic compounds, and/or sulphur-containing compounds.

6. The process according to claim 1, wherein the precursor of molybdenum coordination complex type containing a siloxy ligand is MoO(OSiMe$_3$)CN(CS$_2$-NEt$_2$)$_2$, Mo(=N-(2,6-di-iPrC$_6$H$_3$))(tBu)(=CHtBu)(OSi(OtBu)$_3$), Mo(=S)(=NiPr)(OSitBu$_3$)$_2$, Mo(=O)(OSitBu$_3$)$_4$, Mo(≡N)(OSiPh$_3$)$_3$(C$_6$H$_5$N) or Mo$_2$(OSiMe$_3$)$_6$.

7. The process according to claim 1, wherein the mesoporous matrix is a matrix based on an oxide of at least one element X that is silicon, aluminium, titanium, zirconium, magnesium, lanthanum, cerium or mixtures thereof.

8. The process according to claim 1, wherein the catalyst is prepared by dry impregnation according to a process comprising:
   a) solubilization of the precursor comprising molybdenum and silicon and having at least one sequence of Si—O—Mo bonds of formula I, in a volume of solution corresponding to the pore volume of a preformed mesoporous matrix based on oxide,
   b) impregnation of the preformed mesoporous matrix based on oxide with the solution obtained in a), optional maturation of a solid thus obtained,
   c) optionally drying, calcination and/or steam treatment of the solid obtained at the end of b), at a temperature of 50° C. to 1000° C., and
   d) thermal activation of a solid obtained at the end of c), at a temperature range from 100° C. to 1000° C.

9. The process according to claim 1, wherein the catalyst is prepared according to a process comprising:
   a1) solubilization of the precursor comprising molybdenum and silicon and having at least one sequence of Si—O—Mo bonds of formula I, and a precursor of the mesoporous matrix in an aqueous or hydro-organic solution in the presence of a pore-forming agent so as to form a colloidal solution,
   b1) spray-drying said colloidal solution so as to obtain spherical solid elemental particles incorporating the mesostructured matrix based on oxide and the precursor comprising molybdenum and silicon and having at least one sequence of Si—O—Mo bonds, of formula (I),
   c1) optionally drying, calcination and/or steam treatment of the solid particles obtained at the end of b1), and
   d1) thermal activation of the dry solid particles at the end of c1), at a temperature range from 100 to 1000° C.

10. The process according to claim 1, wherein metathesis is carried out at a temperature of 0 to 500° C.

11. The process according to claim 10, wherein metathesis is cross-metathesis reaction of ethylene with 2-butene, or a reverse reaction converting propylene to a mixture of ethylene and 2-butene.

12. The process according to claim 1, wherein the olefins are linear olefins of formula R$^1$R$^2$C=CR$^3$R$^4$, where R$^1$, R$^2$, R$^3$ and R$^4$, identical or different, are hydrogen or a hydrocarbyl radical of 1 to 20 carbon atoms, or olefins with a cyclic ring structure, the cyclic ring structure having 3 to 20 carbon atoms.

13. The process according to claim 3, wherein the catalyst is prepared by impregnation in excess solution according to the process comprising:
   a') solubilization of the precursor comprising molybdenum and silicon and having at least one sequence of Si—O—Mo bonds, of formula (Ia), in a volume of solution corresponding to between 1.5 and 20 times the pore volume of a preformed mesoporous matrix based on oxide,
   b') impregnation of the preformed mesoporous matrix based on oxide, with the solution obtained in a'), filtration and recovery of the solid, optional maturation of a solid thus obtained,
   c') optionally drying, calcination and/or steam treatment of the solid obtained at the end of b') at a temperature of 50° C. to 1000° C., and
   d') thermal activation of a solid obtained at the end of c') at a temperature of 100° C. to 1000° C.

14. The process according to claim 3, wherein the catalyst is prepared according to a process comprising:
   a1) solubilization of the precursor comprising molybdenum and silicon and having at least one sequence of Si—O—Mo bonds of formula Ia, and a precursor of the mesoporous matrix in an aqueous or hydro-organic solution in the presence of a pore-forming agent so as to form a colloidal solution,
   b1) spray-drying said colloidal solution so as to obtain spherical solid elemental particles incorporating the mesostructured matrix based on oxide and the precursor comprising molybdenum and silicon and having at least one sequence of Si—O—Mo bonds, of formula (Ia),
   c1) optionally drying, calcination and/or steam treatment of the solid particles obtained at the end of b1), and
   d1) thermal activation of the dry solid particles at the end of c1), at a temperature range from 100 to 1000° C.

15. The process according to claim 4, wherein the catalyst is prepared by impregnation in excess solution according to the process comprising:
   a') solubilization of the precursor comprising molybdenum and silicon and having at least one sequence of Si—O—Mo bonds, of formula (Ib), in a volume of solution corresponding to between 1.5 and 20 times the pore volume of a preformed mesoporous matrix based on oxide,
   b') impregnation of the preformed mesoporous matrix based on oxide, with the solution obtained in stage a'), filtration and recovery of the solid, optional maturation of a solid thus obtained,
   c') optionally drying, calcination and/or steam treatment of the solid obtained at the end of b') at a temperature of 50° C. to 1000° C., and
   d') thermal activation of a solid obtained at the end of c') at a temperature of 100° C. to 1000° C.

16. The process according to claim 4, wherein the catalyst is prepared according to a process comprising:
   a1) solubilization of the precursor comprising molybdenum and silicon and having at least one sequence of Si—O—Mo bonds of formula Ib, and a precursor of the mesoporous matrix in an aqueous or hydro-organic solution in the presence of a pore-forming agent so as to form a colloidal solution,
   b1) spray-drying said colloidal solution so as to obtain spherical solid elemental particles incorporating the mesostructured matrix based on oxide and the precursor comprising molybdenum and silicon and having at least one sequence of Si—O—Mo bonds, of formula (Ib),
   c1) optionally drying, calcination and/or steam treatment of the solid particles obtained at the end of b1), and
   d1) thermal activation of the dry solid particles at the end of c1), at a temperature range from 100 to 1000° C.

* * * * *